(12) United States Patent
Califf

(10) Patent No.: US 10,045,725 B2
(45) Date of Patent: Aug. 14, 2018

(54) BLOOD ANALYSIS METHOD AND APPARATUS

(71) Applicant: Hugh Califf, Downers Grove, IL (US)

(72) Inventor: Hugh Califf, Downers Grove, IL (US)

( * ) Notice: Subject to any disclaimer, the term of this patent is extended or adjusted under 35 U.S.C. 154(b) by 302 days.

(21) Appl. No.: 15/153,882

(22) Filed: May 13, 2016

(65) Prior Publication Data

US 2017/0325730 A1    Nov. 16, 2017

(51) Int. Cl.
*A61B 5/00*   (2006.01)
*A61B 5/157*   (2006.01)
*G01N 33/49*   (2006.01)
*B01L 3/00*   (2006.01)
*A61B 5/15*   (2006.01)

(52) U.S. Cl.
CPC ............... *A61B 5/157* (2013.01); *A61B 5/15* (2013.01); *A61B 5/150221* (2013.01); *A61B 5/150236* (2013.01); *A61B 5/150389* (2013.01); *B01L 3/502* (2013.01); *B01L 3/50273* (2013.01); *G01N 33/49* (2013.01); *B01L 2200/026* (2013.01); *B01L 2200/0684* (2013.01); *B01L 2200/141* (2013.01); *B01L 2300/0838* (2013.01); *B01L 2300/0858* (2013.01); *B01L 2300/0861* (2013.01); *B01L 2300/12* (2013.01); *B01L 2300/16* (2013.01); *B01L 2400/0478* (2013.01); *B01L 2400/0487* (2013.01); *B01L 2400/06* (2013.01); *B01L 2400/0688* (2013.01)

(58) Field of Classification Search
CPC ... A61B 5/153; A61B 5/157; A61B 5/150221; A61B 5/150236; A61B 5/150389; A61B 5/150351; A61B 5/150992
See application file for complete search history.

(56) References Cited

U.S. PATENT DOCUMENTS

| | | | |
|---|---|---|---|
| 9,380,973 B2* | 7/2016 | Fletcher | A61M 1/36 |
| 9,597,028 B2* | 3/2017 | Marchiarullo | A61M 1/3403 |
| 9,770,557 B2* | 9/2017 | Pazart | A61B 5/4839 |
| 9,861,745 B2* | 1/2018 | Maier | A61B 5/157 |
| 9,913,604 B2* | 3/2018 | Braig | G16H 20/17 |
| 9,918,702 B2* | 3/2018 | Tariyal | A61B 10/0045 |

\* cited by examiner

*Primary Examiner* — Max Hindenburg
(74) *Attorney, Agent, or Firm* — Fraline Allgaier

(57) ABSTRACT

A capillary chamber for performing chemical and physical analysis using a plurality of whole blood samples is presented. Following a loading of the whole blood samples into a plastic tube, the whole blood samples are distributed into a collection chamber and the capillary chamber has means of adding respective vaccines or similar biological products into each capillary tubes. The whole blood is then analyzed using standard microscopic techniques with sufficient resolution and contrast to record the chemical and physical properties of the blood immediately after withdrawal.

2 Claims, 6 Drawing Sheets

BLOOD ANALYSIS METHOD AND APPARATUS

BACKGROUND OF THE INVENTION

The present invention is related to a blood analysis method and apparatus utilizing a standard microscopic optical system to analyze whole blood subsequent to the administration of a biological product. The invention is concerned with the analysis of blood for proper physical or chemical response to vaccines and other biological products as described below.

The device can be used to analyze the chemical or physical reaction of blood by measuring the electrolytes, antibody levels and cell count in a capillary chamber having a plurality of capillary tubes. Several physical or chemical exams can be conducted using the sample from an initial puncture of the patient or from collected blood samples. The aim is to produce a plurality of aliquots of blood for the on-site hematological examination of the blood.

The administration of any biological product, including vaccines, can create side effects. Some reactions to biological products might be subtle and the patient would eventually recover. For example, a patient might experience redness, warmth, or swelling in the location where the shot was administered (see Table 1 below). It is also known that patients can faint after the administration of a vaccine. Some patients experience severe pain in the shoulder and might have difficulty moving the arm. Most of these side effects are mild and would eventually subside after a few days.

TABLE 1

| VACCINE | SIDE EFFECTS |
| --- | --- |
| Adenovirus | headaches, fever and abdominal pain |
| Anthrax | headaches, fatigue, lump and tenderness |
| DTaP (Diphtheria, Tetanus and Cellular Pertussis) | fussiness, tiredness, vomiting, seizure, fever, coma and brain damage |
| Hepatitis A | soreness, fatigue, loss of appetite and headache |
| Hepatitis B | soreness where the shot was given and temperature of 99.9° F. or higher |
| Hib (Haemophilus influenzae type b) | redness, warmth, or swelling where the shot was given and fever |
| HPV-Cervarix | headache, pain, jerking spells and fainting |
| HPV--Gardasil-9 | fever, headache, redness and swelling |
| Inactivated Influenza | risk of Guillain-Barré Syndrome (GBS), seizure and fainting |

A vaccine, like any medicine, can cause a serious reaction. For example, in the case of the DTaP (Diphtheria, Tetanus and Cellular Pertussis) vaccine shown above, serious allergic reaction can occur in less than 1 out of a million cases. These severe reactions include long-term seizures, coma, lowered consciousness or permanent brain damage. Additional reactions to DTaP have been reported. Moderate reported problems include seizure, jerking or staring (about 1 child out of 14,000), non-stop crying for 3 hours or more (up to about 1 child out of 1,000) high fever, 105 degrees Fahrenheit or higher (about 1 child out of 16,000).

An increased number of scientists have questioned the use of preservatives in vaccines. These are compounds that minimize the growth of microorganisms in a vaccine. In the case of multi-dose vials that are repeatedly used in a clinical setting, a preservative would prevent microbial growth. In most cases, manufacturers add the preservatives in the production stage of the vaccine.

Thimerosal is a mercury-containing preservative that has been widely used in vaccines. Some scientists believe that this preservative can cause autism and other neurodevelopmental disorders. The scientific community agrees that the risk of a vaccine causing serious harm, or death is extremely small and in most cases, severe allergic reactions are believed to occur about once in 1.1 million doses. However, hundreds of millions of people have been vaccinated and it is likely that parental and patient concern would increase with the knowledge that there is a risk of any complication.

In the event of patient or parental concern regarding the side effects or administration of biological products, the invention as described herein can be employed. The improved blood analysis method and apparatus of the present invention would reduce the number of personnel and the amount of equipment needed to perform physical and chemical analysis of blood. The core blood tests would be analyzed and stored in a single location. For example, the complete metabolic profile of a blood sample measuring electrolytes, protein level and liver enzymes could be produced using one or more of the plurality of capillary tubes. A separate capillary tube can be used to measure a complete blood count of a patient including the automatic differential of the white blood cells, neutrophils, lymphocytes, monocytes basophils and eosinophils.

Mandatory rules under the Occupational Safety and Health Agency (OSHA) guidelines must be strictly applied to all collection of blood or other testing samples. The venipuncture site should be cleansed before and after puncture and completed using standard venipuncture techniques. It can be cleaned with required antiseptic such as betadine or 70% isopropyl alcohol.

The administration or handling of this system is to be performed by a trained medical practitioner or scientist. This analysis system would require proficient administration and particular attention to hygiene concerns before and after use of the product. The scientist or medical practitioner must pay keen attention to the appropriate method for the collection and storage of blood for analysis using the described capillary chamber.

This system is also suitable for mass production. It features a simple design and construction that provides for easy handling and appropriate disposal after blood collection and analysis.

BRIEF SUMMARY OF THE INVENTION

It is therefore an objective of the present invention to provide a blood analysis method and apparatus utilizing a standard microscopic system to analyze whole blood subsequent to the administration of a biological product. wherein each patient receives an injection and whole blood is collected and analyzed for quantitative, semi-quantitative or qualitative results.

An objective of the present invention is to provide a whole blood analysis of a plurality of vaccines and additional biological products in a single analysis chamber.

Another objective of the present invention is to perform core hematological, biochemical and immunological testing in a single analysis chamber.

Another objective of the present invention is to produce core hematological, biochemical and immunological testing results of whole blood in the same facility or clinical location.

Still another objective of the present invention is to provide an analysis chamber that is simple and economically feasible to manufacture.

DETAILED DESCRIPTION OF THE INVENTION

The detailed description is for illustrative purposes and does not limit the scope of the present invention. The embodiments described below provide sufficient information to enable a person having ordinary skill in the art to practice the invention. It should be understood that other embodiments could be practiced with multiple variations without departing from the scope of the invention.

The blood analysis method and apparatus 10 as described herein can be performed by medical technologists, medical laboratory scientists, nurses, physicians who are specialized in hematology or physicians who are trained to operate the equipment as described herein. The hematological assessments can be conducted to study blood conditions including anemia, hemophilia and bleeding disorders. Arterial, capillary or venous blood, bone marrow and cord blood can be used for a plurality of physical and chemical assessments. Hematological assessments utilizing tissue or blood samples relating to reticuloendothelial systems (bone marrow, spleen or liver), blood transfusions (blood plasma), red blood cell sampling for testing (hemoglobin, glycolysis, chemical metabolism or erythropoiesis) and additional tissue or blood sampling can be used.

Figure 1:
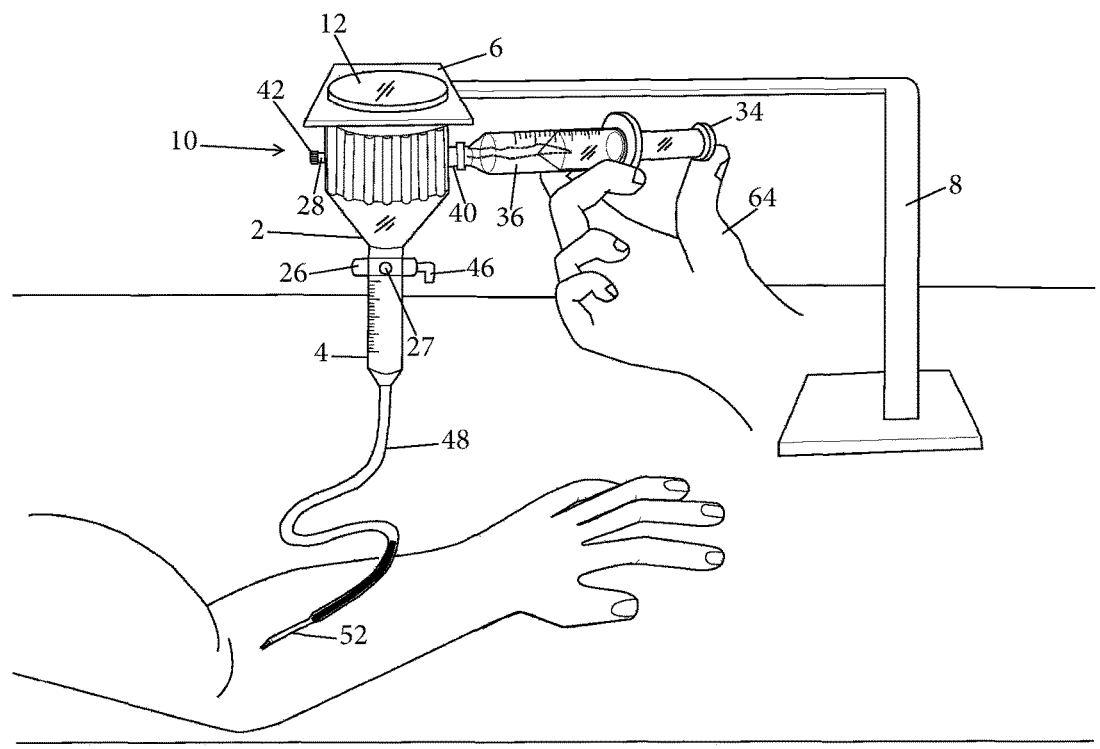
FIG. 1 is a perspective view of the blood analysis apparatus and the biological product being administered.
Figure 2:
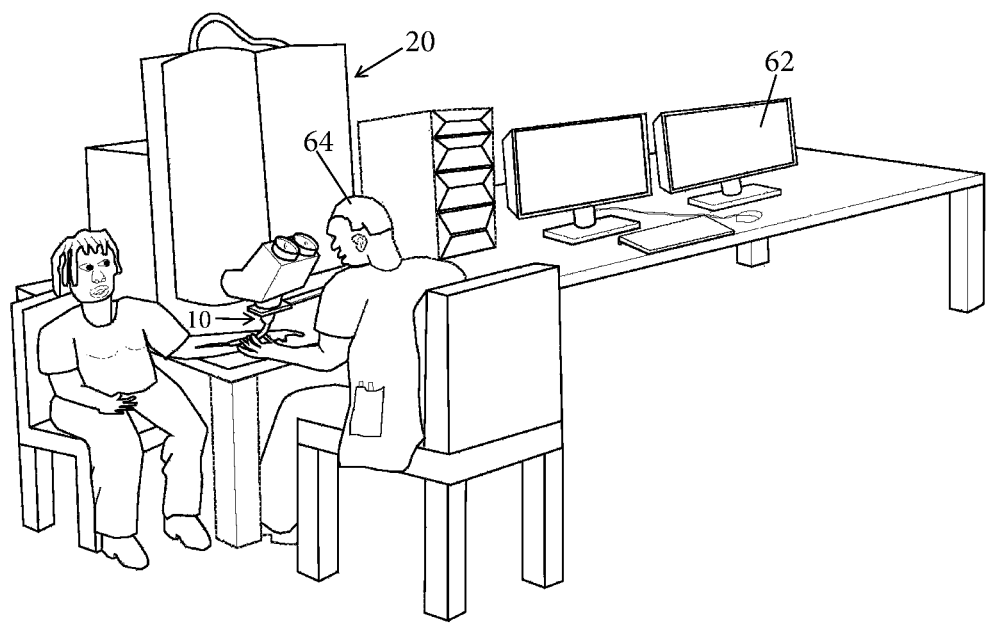
FIG. 2 illustrates an exemplary representation of a patient being injected and the whole blood sample being analyzed.
Figure 3:
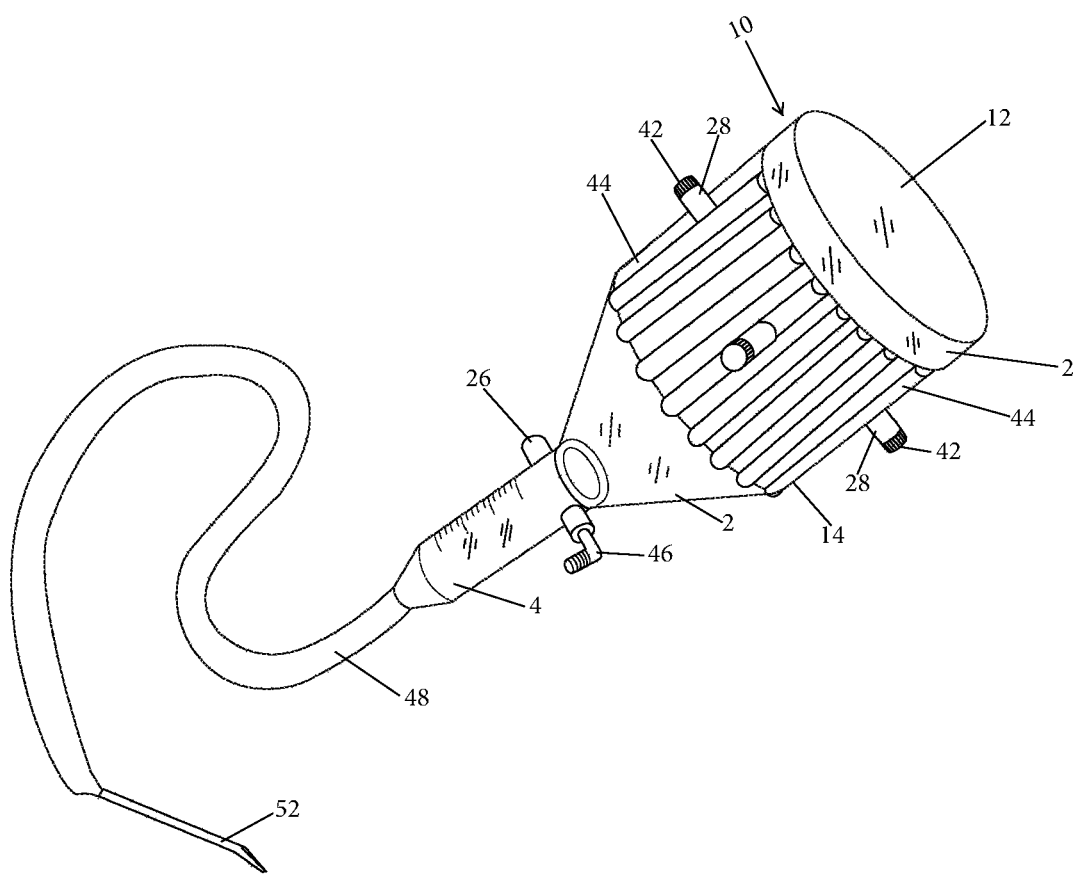
FIG. 3 is a perspective view of the blood analysis apparatus.
Figure 4:
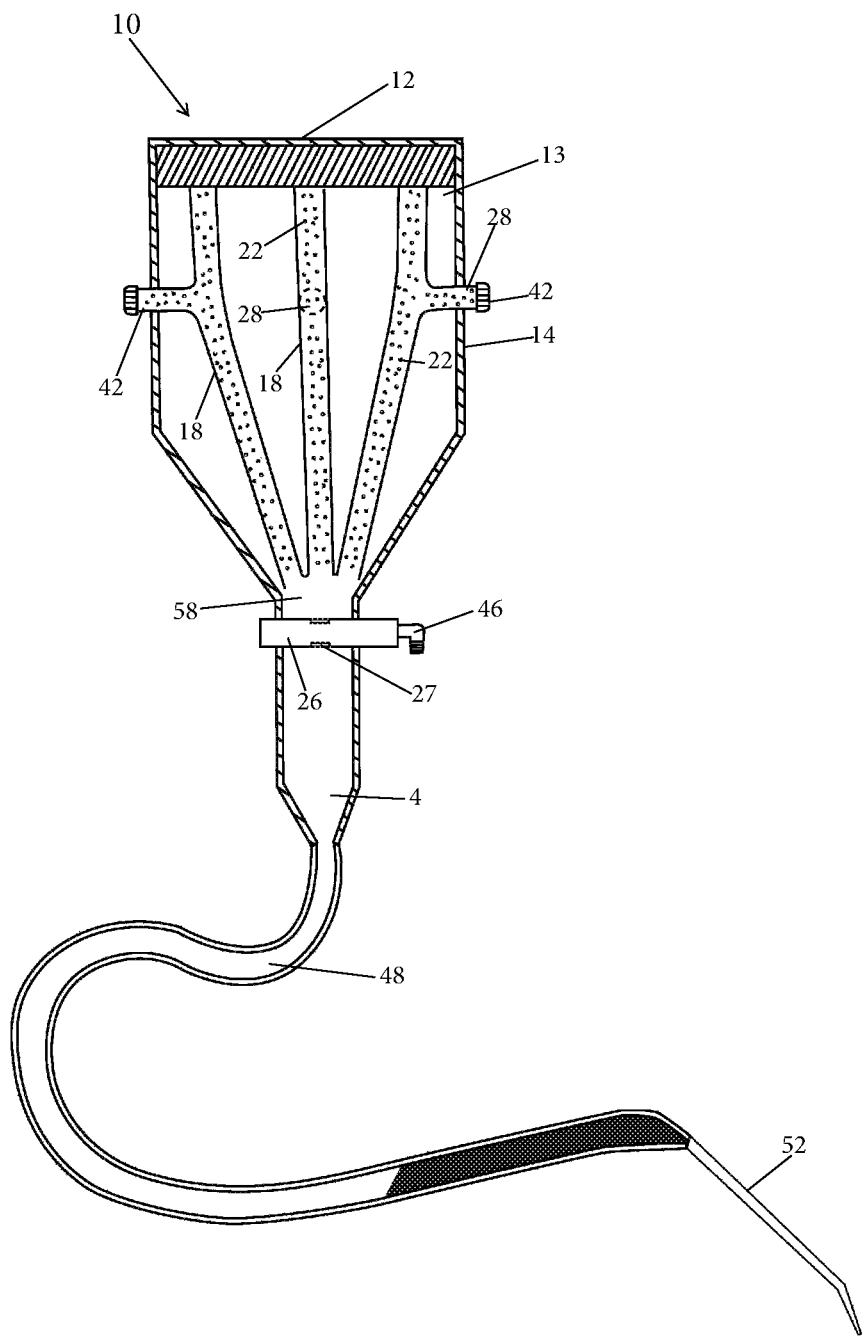
FIG. 4 is a cross-sectional view of the blood analysis apparatus.
Figure 5:
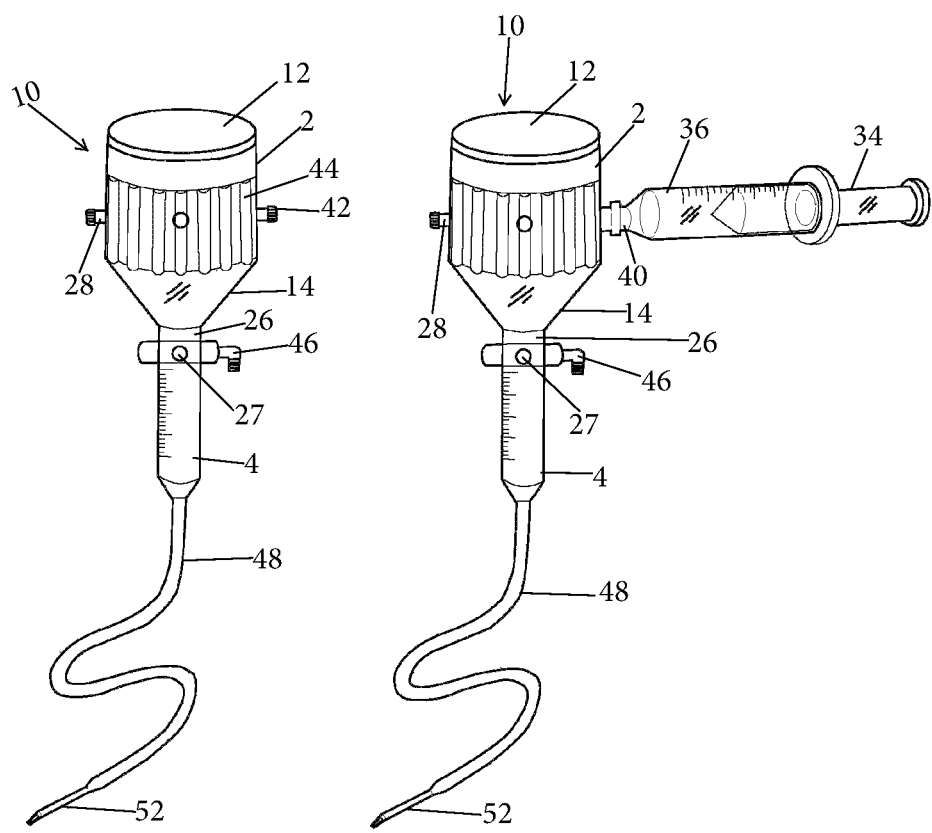
FIG. 5. illustrates a plurality of the blood analysis apparatus in accordance with the present invention.
Figure 6:
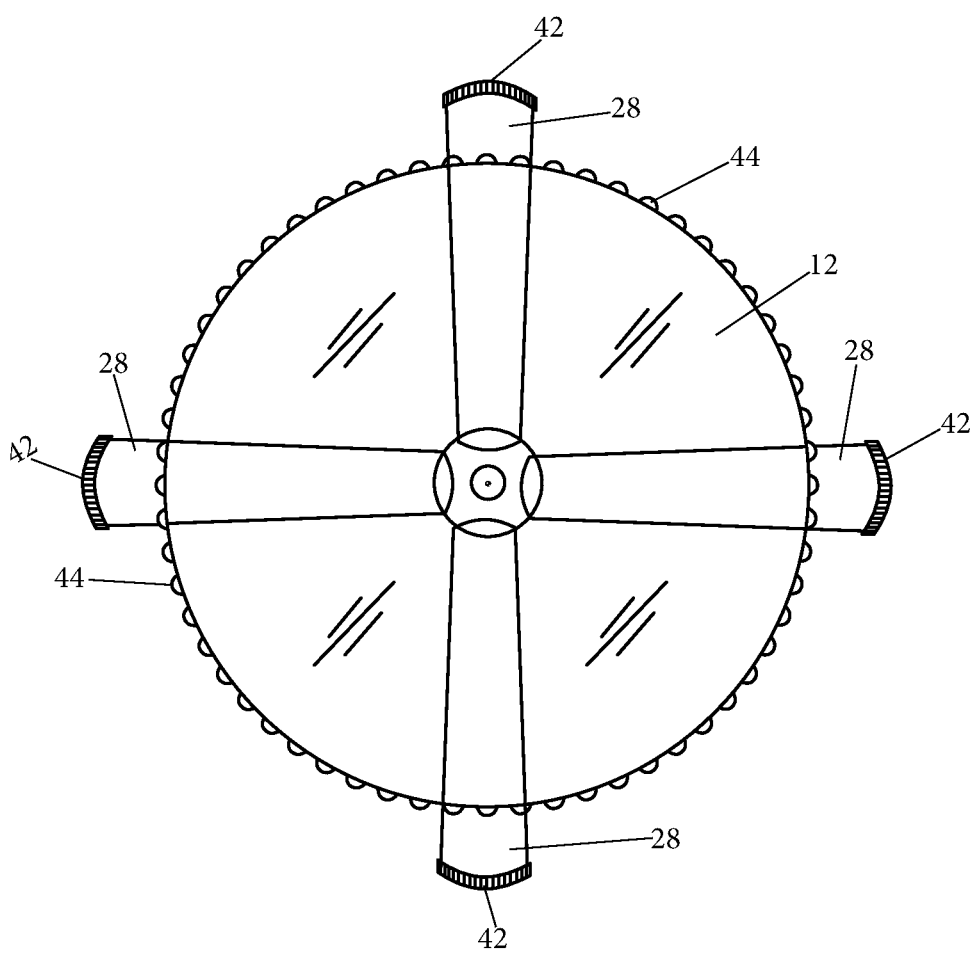
FIG. 6 is an exploded top view of the capillary chamber and the plurality of capillary tubes.

Referring now to the drawings, FIG. 1 shows a blood analysis method and apparatus 10 comprising a capillary chamber 2, a collection chamber 4, and a chamber station 8. FIG. 2 shows an exemplary microscopic system 20 that can be used. Standard microscopic systems 20 can include scanning electron microscopes, transmission electron microscopes or compound light microscopes. The microscopic system 20 used for a blood analysis as described herein will depend on the clarity desired for a specific test or blood specimen.

FIGS. 3-6 show the capillary chamber 2 together with the additional parts as described herein functioning as an overall whole blood analysis system. The microscopic system 20 as required herein has the resolving and contrast power to view, clearly examine and analyze whole blood. It is further enabled to detect the progressive interaction of the blood and biological product 36 to reproduce images and produce results of each capillary tube 18 on enlarged screens 62.

Biological products 36 are medical products that can be used to treat a specific medical condition. These can include vaccines, blood or blood products for transfusion, allergenic extracts such as allergy shots, gene therapies, cellular therapies or tests to screen potential blood donors for infectious diseases such as chicken pox, herpes, human immune deficiency virus (HIV) or zika virus.

The capillary chamber 2 has a top wall 12, an inner cavity 13 and an outer wall 14. The top wall 12 is preferably prepared by the manufacturer during the production of the blood analysis apparatus 10. The inner cavity 13 houses a plurality of capillary tubes 18 and is coated with an anticoagulant agent 22. The anticoagulant agent 22 prevents coagulation of the whole blood prior to analysis using the microscopic system 20. Heparin and various types of heparin salts are popular types of anticoagulant agents 22 that can be used to prevent blood or plasma clotting in the capillary tubes 18.

The top wall 12 of the capillary chamber 2 is a thin flat piece of glass that is less than one millimeter thick and allows for physical and chemical analysis of the whole blood. The top wall 12 is made from optical quality materials such as soda lime glass, borosilicate glass, specialty plastics or fused quarts. It is permanently affixed to the top perimeter of the capillary chamber 2 to prevent the entrance of air and contaminants. The capillary tubes 18 extend in a downward position from the top wall 12 toward the capillary valve 26 and valve opening 27. The downward extending plurality of capillary tubes 18 form a capillary spout 58 that is arranged to reduce the risk of formation of air bubbles in the capillary tubes 18.

The plurality of capillary tubes 18 is used for physical or chemical analysis of more than one biological product 36 in each capillary tube 18. The capillary valves 28 radiate outward from the exterior wall of the capillary chamber 2 and are sized to receive the tips 40 of a standard syringe 34. The capillary valves 28 are located at different circumferential locations on the exterior of the capillary chamber 2. The capillary valves 28 have capillary caps 42 to prevent air from entering the capillary chamber 2 after a biological product 36 has been administered.

The outer wall 14 has horizontal grooves 44 on the surface and allows the user to properly engage the outer wall 14 while administering the biological product 36. The capillary valve 26 has an actuating member 46 facilitating the flow of whole blood into and out of the capillary chamber 2. The syringe 34 is used to administer the biological product 36 and to draw the whole blood upwards into the capillary tube 18. The syringe 34 is further compressed to discharge the biological product 36 and in union with the osmotic force of the capillary valve 26 allow the whole blood to flow into the capillary tubes 18.

The collection chamber 4 has a plastic tube 48, a needle 52 and an anticoagulant agent 22 embedded on the inner wall of the collection chamber 4 in order to prevent coagulation of the whole blood prior to analysis. The needle 52 is cohesively joined to the plastic and is of conventional size and construction in order to facilitate the rapid flow of whole blood into the collection chamber 4. The needle 52 is connected to the plastic tube 48 by assembly or by the administrator 64. After injection, the volume of whole blood is increased automatically by the prevailing pressure gradient that allows the blood to flow through the needle 52 and into the capillary tube 18.

The chamber retainer 6 holds the capillary chamber 2 in place and retracts easily into the capillary chamber 2. The chamber retainer 6 increases the effectiveness of the microscopic resolution of the microscopic system 20 by moving the top wall 12 of the capillary chamber 2 in order to obtain a focal point of view and allow examination of a specific capillary tube 18 or to obtain a desired scanning location. The chamber station 8 is adapted to hold the chamber retainer 6. The whole blood is stored in the collection chamber 4 and an aliquot of the whole blood is transferred to the capillary chamber 2 for analysis.

The geometry and size of the apparatus 10 including the length and diameter of the needle 52 will vary by the type of application that is desired. The blood analysis method and apparatus 10 can be combined with routine biochemical and hematological analyses methods for qualitative analysis. Common routine biochemical analyses methods include serum chemistries, liver function tests, complete blood count analysis, blood gas analysis, toxicology screenings and biochemical strips. The apparatus 10 cannot be removed for sterilization or reused and must be properly discarded after use.

What is claimed is:

1. A blood analysis apparatus comprising:
   a microscopic system, a capillary chamber, a collection chamber, and a chamber station;
   said capillary chamber having a top wall, an inner cavity and an outer wall; said inner cavity having a plurality of capillary tubes; said inner cavity having an anticoagulant agent on the inner wall of said inner cavity in order to prevent coagulation of whole blood prior to analysis by said microscopic system; said top wall being a thin flat piece of glass that is less than one millimeter thick and allowing for hematological assessments using said microscopic system; said top wall being made from optical quality materials; said top wall being permanently affixed to the top perimeter of said capillary chamber to prevent the entrance of air and contaminants; said capillary tubes extending in a downward position from said top wall; said capillary tubes extending downwards to a valve opening and forming a capillary spout; said capillary spout being arranged to reduce the risk of formation of air bubbles in said capillary tubes; said capillary tubes having capillary valves being adapted to receive a syringe; said capillary tubes being used for analysis of more than one biological product in the individual capillaries; said capillary valves radiating outward from the exterior wall of said capillary chamber; the opening of said capillary valves being sized to receive the tips of said syringe; said capillary valves being located at different circumferential locations on the exterior of said capillary chamber; said outer wall housing said capillary valves on the outer perimeter of said outer wall; said capillary valves having capillary caps to prevent air from entering said capillary chamber after said biological product has been administered; said outer wall having horizontal grooves on the surface and allowing the user to properly engage said outer wall while administering said biological product; said capillary valves having an actuating member facilitating the flow of said whole blood into and out of said capillary chamber; said syringe being used to administer said biological product and to draw said whole blood upwards into said capillary tube; said syringe being further compressed to discharge said biological product drug and in union with the osmotic force of said capillary valves allowing said whole blood to flow into said capillary tubes;
   said collection chamber having a plastic tube and a needle and having said anticoagulant agent embedded on the inner wall of said collection chamber in order to prevent coagulation of said whole blood prior to analysis; said needle being cohesively jointed to said plastic tube; said needle being of conventional size and construction in order to facilitate the rapid flow of whole blood into said collection chamber;
   said chamber station having a chamber retainer, said chamber retainer holding said capillary chamber in place and retracts easily into said capillary chamber; said chamber retainer increasing the effectiveness of the microscopic resolution of said microscopic system by moving said top wall of said capillary chamber in order to obtain a focal point of view and allow examination of a specific capillary or to obtain a desired scanning location;
   said chamber station being adapted to suspend said capillary chamber;
   said whole blood being stored in said collection chamber and an aliquot of said whole blood being transferred to said capillary chamber for analysis.

2. The analysis apparatus of claim 1 wherein said blood analysis apparatus is used for routine biochemical and hematological analyses methods for qualitative analysis.

* * * * *